(12) United States Patent
De Duonni et al.

(10) Patent No.: US 11,959,662 B2
(45) Date of Patent: Apr. 16, 2024

(54) INDOOR AND OUTDOOR NANO AIR PURIFIER AND SYSTEM COMPRISING SAID PURIFIER

(71) Applicant: DIRAC S.R.L., Rome (IT)

(72) Inventors: Davide De Duonni, Rome (IT); Federico Mallia, Rome (IT)

(73) Assignee: DIRAC S.R.L., Rome (IT)

( * ) Notice: Subject to any disclaimer, the term of this patent is extended or adjusted under 35 U.S.C. 154(b) by 0 days.

(21) Appl. No.: 17/294,900

(22) PCT Filed: Nov. 5, 2019

(86) PCT No.: PCT/IB2019/059491
§ 371 (c)(1),
(2) Date: May 18, 2021

(87) PCT Pub. No.: WO2020/104878
PCT Pub. Date: May 28, 2020

(65) Prior Publication Data
US 2022/0016305 A1 Jan. 20, 2022

(30) Foreign Application Priority Data
Nov. 19, 2018 (IT) ........................ 102018000010423

(51) Int. Cl.
*A61L 9/20* (2006.01)
*B01D 53/00* (2006.01)
(Continued)

(52) U.S. Cl.
CPC .............. *F24F 8/167* (2021.01); *A61L 9/205* (2013.01); *B01D 53/007* (2013.01);
(Continued)

(58) Field of Classification Search
None
See application file for complete search history.

(56) References Cited

U.S. PATENT DOCUMENTS 9,352,829 B2    5/2016  Sottiaux et al.
2012/0275960 A1*  11/2012  Seck ...................... A62B 15/00
                                                        422/121
(Continued)

FOREIGN PATENT DOCUMENTS

CN    203550055    4/2014
CN    106322506    1/2017
(Continued)

OTHER PUBLICATIONS

No name—'061-KR20090013061U—original and translated document (Year: 2009).*
(Continued)

Primary Examiner — Jelitza M Perez
(74) Attorney, Agent, or Firm — NIXON & VANDERHYE

(57) ABSTRACT

Indoor and outdoor air purifier including:—a fan for suctioning air and conveying it into—an air treatment duct suitable to disintegrate the toxic and pollutant components present in the air and then reintroducing the air, purified by now, into the external environment through one of the grids; within the duct, at least the following being installed: ○ filters in any alveolar ceramic alloy treated with a titanium dioxide $TiO_2$ nano-coating suitable to disintegrate the pollutant substances by a photocatalytic process activated thanks to ○ LED lights, each of which installed in proximity to a corresponding filter, suitable to start the pollutant molecules disintegration photocatalytic process, reintroducing only the harmless substances into the atmosphere.

18 Claims, 3 Drawing Sheets

(51) Int. Cl.
  *B01D 53/86* (2006.01)
  *B01D 53/88* (2006.01)
  *F24F 8/167* (2021.01)
  *F24F 8/20* (2021.01)

(52) U.S. Cl.
  CPC ..... *B01D 53/8609* (2013.01); *B01D 53/8615* (2013.01); *B01D 53/8628* (2013.01); *B01D 53/8631* (2013.01); *B01D 53/8634* (2013.01); *B01D 53/8637* (2013.01); *B01D 53/864* (2013.01); *B01D 53/8662* (2013.01); *B01D 53/8668* (2013.01); *B01D 53/885* (2013.01); *F24F 8/20* (2021.01); *A61L 2209/111* (2013.01); *A61L 2209/12* (2013.01); *A61L 2209/14* (2013.01); *A61L 2209/15* (2013.01); *B01D 2255/20707* (2013.01); *B01D 2255/802* (2013.01); *B01D 2257/2064* (2013.01); *B01D 2257/302* (2013.01); *B01D 2257/304* (2013.01); *B01D 2257/306* (2013.01); *B01D 2257/404* (2013.01); *B01D 2257/406* (2013.01); *B01D 2257/502* (2013.01); *B01D 2257/7025* (2013.01); *B01D 2257/7027* (2013.01); *B01D 2258/06* (2013.01); *B01D 2259/802* (2013.01)

(56) References Cited

U.S. PATENT DOCUMENTS

| | | | |
|---|---|---|---|
| 2014/0252157 A1* | 9/2014 | Sottiaux | B64C 27/35 244/17.11 |
| 2018/0050124 A1 | 2/2018 | Lee | |

FOREIGN PATENT DOCUMENTS

| | | | | |
|---|---|---|---|---|
| CN | 106440090 | | 2/2017 | |
| CN | 107036158 | | 8/2017 | |
| CN | 107975876 | | 5/2018 | |
| CN | 108278691 | | 7/2018 | |
| CN | 108568213 A | * | 9/2018 | ......... B01D 46/0024 |
| EP | 1 281 431 | | 2/2003 | |
| JP | 2005-180870 | | 7/2005 | |
| JP | 2018-132246 | | 8/2018 | |
| KR | 20090013061 U | * | 12/2009 | |
| KR | 101198923 B1 | * | 7/2012 | ............ B01D 39/14 |
| KR | 10-1198923 | | 11/2012 | |
| KR | 101198923 B1 | * | 11/2012 | |

OTHER PUBLICATIONS

Wu—CN102039012A—original and translated document (Year: 2011).*
No name—'923-KR101198923B1—translated document (Year: 2012).*
Deng et al. CN108568213A—translated document (Year: 2018).*
No name—'061-KR20090013061U—translated document (Year: 2009).*
KR101198923B1—tranlated document (Year: 2012).*
International Search Report for PCT/IB2019/059491 dated Jan. 28, 2020, 4 pages.
Written Opinion of the ISA for PCT/IB2019/059491 dated Jan. 28, 2020, 6 pages.

* cited by examiner

INDOOR AND OUTDOOR NANO AIR PURIFIER AND SYSTEM COMPRISING SAID PURIFIER

This application is the U.S. national phase of International Application No. PCT/IB2019/059491 filed Nov. 5, 2019 which designated the U.S. and claims priority to IT Patent Application No. 102018000010423 filed Nov. 19, 2018, the entire contents of each of which are hereby incorporated by reference.

BACKGROUND OF THE INVENTION

Field of the Invention

The present invention regards the field of anti-pollution systems aimed at purifying air. More in detail, the purifier in question is designed both for indoor environments and outdoor environments or for purifying air in environments subject of particular standards such as schools and hospitals.

Description of the Related Art

Global pollution caused by combustion of fossil materials is a widely known fact same case applying to the negative impact on the environment and on the health of humans and animals.

The negative impact thereof also reflects in the dirt that accumulates on town buildings and monuments, forcing the administrations of big cities to take action subsequently and, simultaneously, to find solutions for the future.

As concerns the quality of external air, there seems to be no existing technologies with immediate effects. Rather, there is an ongoing attempt to find possible long-term solutions which, in an indefinite future, could allow to reduce the pollutant substances present in the air we breathe.

On the other hand, progress has been made as concerns indoor air, especially in environments exposed to high risk of bacterial contamination such as hospitals and, more generally, public and work environments.

However, the technologies used up to date reveal criticalities, the most serious of which are listed below:
- the pollutant substances are not disintegrated but only withheld in the filters, hence not guaranteeing the total absence of the pollutant in the air but just reducing the percentage thereof;
- they require a lot of maintenance and periodic replacement of the components;
- they are not capable of withholding all types of pollutants;
- usually, they are large in size, expensive and require a specific installation that is to be designed and installed, increasing the costs thereof;
- the disposal of the filters creates more pollution, configuring all these technologies as local and temporary solutions;
- they are not capable of processing large volumes of air and thus they are limited to closed environments and with limited flow rates.

Some international patents specifically regard air purification systems which however do not resolve all the aforementioned problems.

By way of example, some patents of Chinese origin, such as CN107036158, regard air purification systems designed for outdoor environments. However, they require complex systems that inflate the investment required for the installation thereof.

However, the nano-coatings have been known for quite some time and they are also subject, besides of several studies, of numerous patents which however regard fields of application different from the one of the present invention. An example is the United States patent n° U.S. Pat. No. 9,352,829 which claims the coating of the wings of an aircraft with a nano-protection wax. The object of this patent is to protect the wings of the aircraft against harmful environments.

On the other hand, the object of the present invention is to provide a new and innovative air purification system that can be installed both outdoors and indoors thus resolving all the criticalities described previously and thus reducing the installation times and costs.

SUMMARY OF THE INVENTION

According to the present invention, provided is a purifier, possibly integrated in the outdoor and indoor air purification system, capable of effectively overcoming the problems outlined above.

Advantageously, besides the air for indoor and outdoor environments, the purifier of the present invention is suitable to suction the air of any environment, purify it of pollutant substances, bacteria and odours, and release it into the atmosphere once again. More in detail, the purifier is suitable to disintegrate at least the following pollutant and toxic substances:
- inorganic compounds such as: NOX; SOX; CO; $NH_3$; $CH_3S$; $H_2S$;
- chlorinated organic compounds such as: $CH_2Cl_2$; $CHCl_3$; $CCl_4$; 1,1-$C_2H_4Cl_2$; 1,2-$C_2HaCl_2$; 1,1,1-$C_2H_3Cl_3$; 1,1,2-$C_2H_3Cl_3$; 1,1,1,2-$C_2H_2Cl_4$; 1,1,2,2,-$C_2H_2Cl_4$; 1,2-$C_2H_2Cl_2$; $C_2HCl_3$; $C_2Cl_4$; dioxins; chlorobenzene; chlorophenol;
- organic compounds such as: $CH_3OH$; $C_2H_5OH$; $CH_3COOH$; $CH_4$; $C_2H_6$; $C_3H_8$; $C_2H_4$; $C_3H_6$; $C_6H_6$; phenol; toluene; ethylbenzene; o-xylene; m-xylene; phenanthraquinone;
- pesticides such as: tradimefon; pirimicarb; asulam; diazinon; MPMC; atrazine;
- bacteria;
- virus.

Through photocatalysis, activated by the technological components to be addressed hereinafter, the aforementioned molecules are advantageously broken down into limestone, sodium nitrates and nitrites, calcium nitrates and nitrites, sodium carbonates and salts. All these are substances completely harmless for the environment and living beings and which, should they deposit in the purifier, can be easily washed away even by rain or—in the smaller versions of the purifier—with a wet towel.

Outside, the purifier has a covering guard, that can be opened to guarantee access to the internal components. An upper grid and a lower grid which allow the circulation of air in the purifier are present respectively above and beneath the guard.

The structure is completed by a base, a lid and an internal structure made of supports which protect and stabilise the object.

Preferably but not limitedly, the purifier will be cylindrical-shaped.

An axial fan which suctions the air from one of the two grids and introduces it into the purification duct which treats it and, subsequently, reintroduces it clean into the atmosphere flowing through another grid, is advantageously installed in the structure of the purifier. A plurality of LED lights, each one of which is coupled to a relative purification filter, are advantageously installed in the air treatment duct.

Contrary to the common filters of the purification plants available on the market up to now, the filters of the present invention disintegrate the molecules thanks to their titanium dioxide ($TiO_2$) nano-coating, which, activated with the LED light gives forth to the photocatalytic process of disintegrating the pollutants.

Advantageously, the filters are made of alveolar ceramic alloy so as to maximise the contact surface between the filter and the air that flows through it, and thus make the entire purifier more effective.

A plurality of pairs of filter-LED light so that the external air—flowing through several filters—is purified, is advantageously provided for.

All internal and external surfaces of the purifier, except for those of the filters, are advantageously treated using common protection nano-coatings to protect them against external attacks and deterioration due to the normal wear of the materials exposed to atmospheric agents.

Upon installing the purifier in the open or closed, public or private site, whose air quality is intended to be improved, it will be sufficient to connect it a normal source of electric power to activate the continuous operation cycle thereof.

For example, the purifier in question may be of dimensions suitable to be placed on a bedside table, next to the bed of any home, or on a common office desk, thus improving the quality of the domestic air or of the work environment air and thus avoiding the contamination of flu and other seasonal illnesses, besides diseases of more infectious form.

The guard may be advantageously made transparent or translucent, so as to externally show the internal LED lights and thus, not only contribute to the aesthetic appeal of the object, but also make it useful with a table lamp or abat-jour.

In order to accentuate this function, the purifier of the present invention can also be advantageously provided with at least one external LED light, suitable to light up simultaneously with the switching on of the purifier or separately by means of a special switch, suitable to make the purifier useful as a lamp too.

In other even more advantageous versions of the present invention, the purifier in question may be provided with a photovoltaic panel superimposed or integrated on the lid to improve the effectiveness thereof possibly achieving energy self-reliance. A remote-settable timer, suitable to actuate and block said fan at pre-established times, may further be provided for. Should one intend to computerise and monitor the efficiency of the purifier subject of the present invention from a remote position, it can be advantageously integrated in a system comprising one of said purifiers, possibly provided with a timer, and a sensor suitable to monitor the volume of treated air. The sensor, in this embodiment, is suitable to communicate the detected data to a dedicated server which stores the data in the memory connected thereto. The possibility of installing, at each filter of each purifier, a sensor suitable to detect the amount of toxic and/or pollutant substances withheld in said filter. Even said sensors advantageously send the detected data to the server.

Thanks to these components, a manager user of the purification system may, by accessing said dedicated server using pre-set credentials, know in real time the effectiveness of the system and also view the data records.

It will also be possible to adjust the volume of treated air up to the maximum allowed by the capacity of the purifier and schedule works regarding the maintenance and replacement of the filters depending on the residual effectiveness thereof.

The advantages provided by the present invention will be clear in light of the description outlined up to now. Furthermore, they will be more apparent due to the attached figures and relative detailed description.

BRIEF DESCRIPTION OF THE DRAWINGS

The invention will be described hereinafter in at least one preferred embodiment, provided by way of non-limiting example, with reference to the attached figures, wherein.

DESCRIPTION OF THE PREFERRED EMBODIMENTS

Now, the present invention will be illustrated purely by way of non-limiting or non-binding example, with reference to the figures illustrating some embodiments regarding the present inventive concept.

Figure 1:
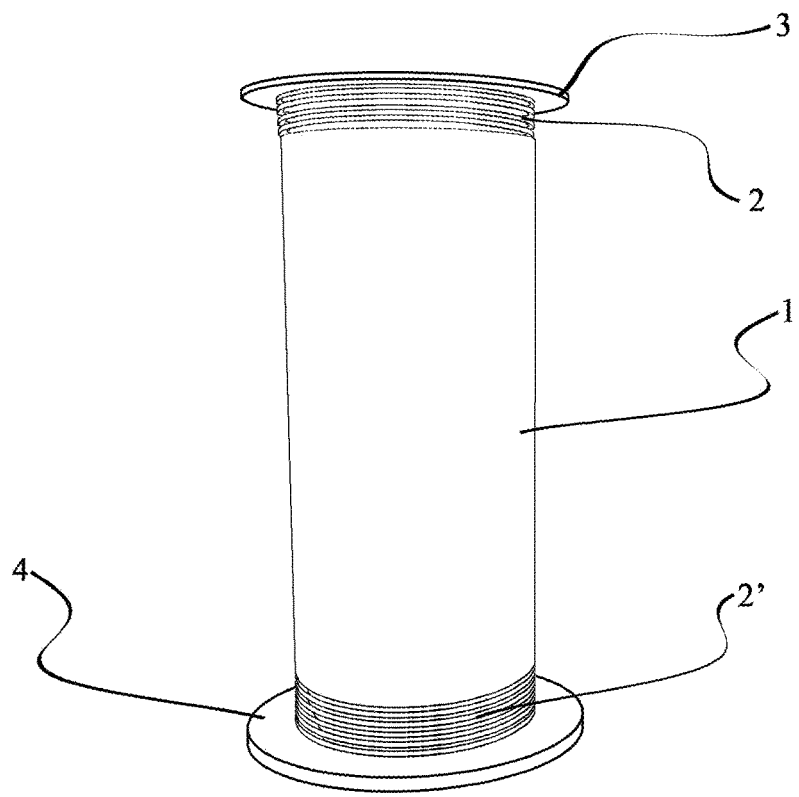
FIG. 1 shows outer structure of the purifier in a cylindrical embodiment in which the base 4, the lid 3, the guard 1 and the two upper and lower air circulation grids 2-2' are visible.

The outer aspect of the preferred embodiment of the purifier of the present invention is shown with reference to FIG. 1.

It is cylindrical-shaped, with an upper protection lid 3 and a base 4 which allows the purifier to be integrally joined to the ground.

Figure 2:
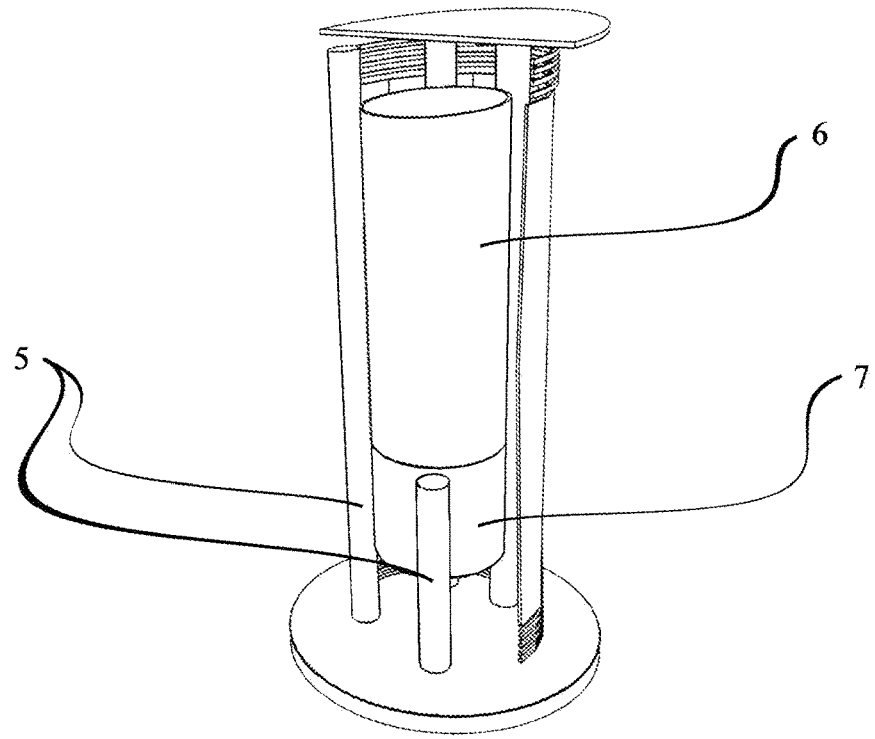
FIG. 2 shows a cross-section of the same object of the previous FIG. 1 in which the inner supports 5, the duct 6 and the fan 7 arranged beneath, are visible.
Figure 3:
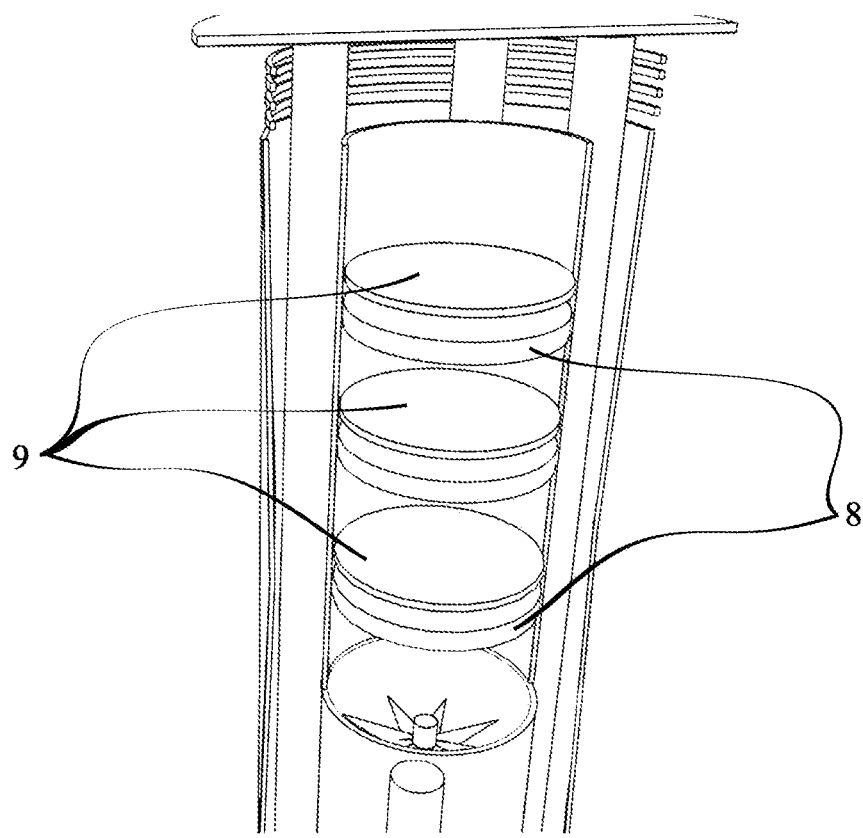
FIG. 3 shows, more in detail, the internal components of the duct 6 consisting of a plurality of filters 8 and LED lights 9.

The lateral surface of the cylinder consists of an openable protection guard 1 and of an upper grid 2 with rings identical to a lower grid 2' with rings. Internally, as shown in FIG. 2, a support system 5 holds an air treatment duct 6 and an axial fan 7 which suctions air from the external conveying it into the duct 6, in the position previously provided for.

In order to eliminate the potentially toxic substances, the external air which is conveyed in the treatment duct 6, flows through at least three filters 8 coupled with LED lights 9. Said filters 8 are made of alveolar ceramic alloy, so as to optimise the volume/surface ratio and thus make system efficient to the utmost. Said filters 8 are subsequently treated with Titanium Dioxide ($TiO_2$) nano-coatings, which, when impacted by the LED light, start a photocatalysis process which disintegrates pollutant substances, toxic substances, bacteria and virus into salts and other harmless substances.

All the other surfaces of the purifier, except for those of the filters, are treated with protection nano-coatings.

Due to its ease of installation and operation, the purifiers of the present invention are suitable to be installed outdoors, preferably in urban centres more subject to pollution, places particularly exposed to bacterial risks, such as workplaces, schools and hospitals.

Figure 4:
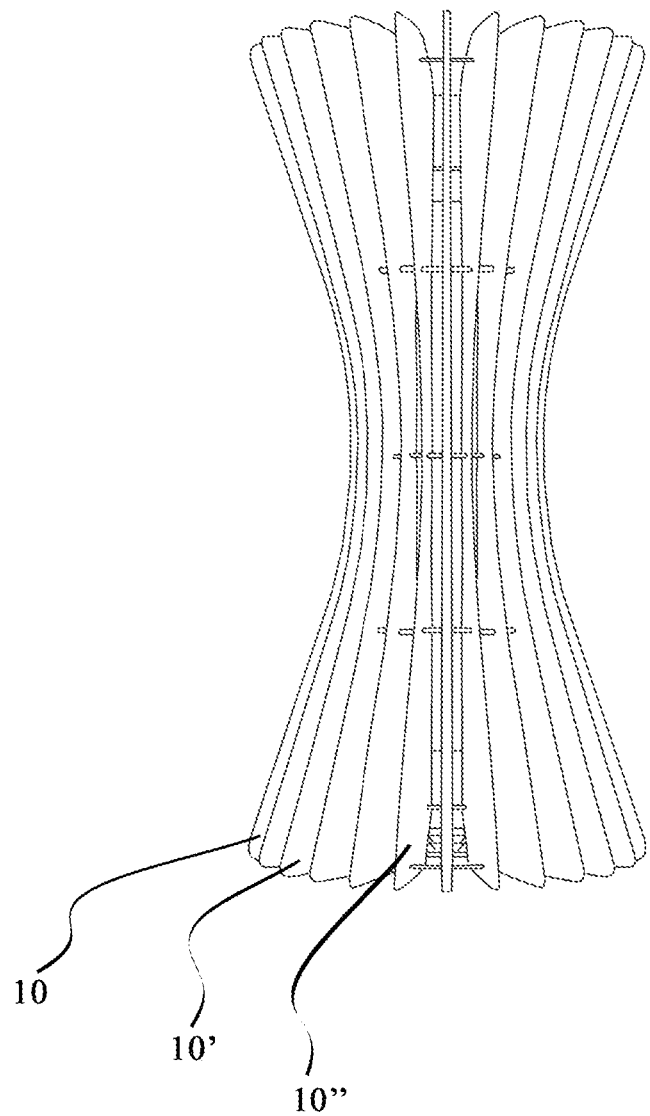
FIG. 4 shows a table version of the purifier of the present invention in which the light coming from the interior of the device thanks to the outer covering with longitudinal strips 10-10'-10"- . . . , can be seen.

An example of such variants is obtained by manufacturing the purifier in the "table" version, i.e. small dimensions, and possibly provided with technical/aesthetic solutions like in the example indicated in FIG. 4. In this case, the purifier also serves as a table lamp thanks to the fact that the outer guard 1 is transparent and covered with longitudinal strips 10-10'-10" which modulate and filter the light coming from the LED lights 9 inside the purifier. The use currently deemed most convenient for a purifier thus made, is the office use, i.e. placing a purifier for each desk of a work environment. Besides being aesthetically appealing, such purifiers are sources of lighting for the desk and they purify the air breathed by all employees of an office from bacteria, virus and other impurities according to the same methods described above.

Lastly, it is clear that the invention described up to now may be subjected to modifications, additions or variants obvious to a man skilled in the art, without departing from the scope of protection outlined by the attached claims.

The invention claimed is:

1. An indoor and outdoor air purification system, comprising:
    at least one indoor and outdoor purifier, suitable to suction air of any environment, purify the air of pollutant substances, bacteria or odours, the air purifier comprising
    an air treatment duct (6) having an interior surface which is a closed arcuate interior surface and an exterior surface which is a closed arcuate exterior surface, the interior surface defining an air treatment path with a suction inlet and a discharge outlet,
    an air suctioning axial fan (7), suitable to suction air from an external environment, to convey the air into the suction inlet of the air treatment duct (6) to disintegrate the toxic and pollutant components present in the air and then reintroducing the air, purified now, via the discharge outlet into the external environment,
    a plurality of LED lights (9) located within an interior of the air treatment duct (6), each of the plurality of LED lights (9) having a closed arcuate perimeter,
    at least a plurality of filters (8) installed in said treatment duct (6) such that external air conveyed in the air treatment duct (6) flows through the at least the plurality of filters (8), each of the plurality of filters (8) having a closed arcuate perimeter, each of the plurality of filters (8) being coupled to one of the plurality of LED lights (9), each of the plurality of filters (8) being made of any alveolar ceramic alloy treated with a titanium dioxide $TiO_2$ nano-coating suitable to disintegrate the pollutant substances by a photocatalytic process activated by the plurality of LED lights (9),
    wherein each of the plurality of LED lights (9) is installed in proximity to and coupled to at least corresponding one of the plurality of filters (8) with the closed arcuate perimeter of each of the plurality of LED lights (9) being located above the closed arcuate perimeter of the corresponding one of the plurality of filters (8) such that each of the plurality of LED lights (9) suitably activates the corresponding one of the plurality of filters (8) to start the pollutant molecules disintegration photocatalytic process, reintroducing only the harmless substances into the external environment;
    at least one sensor installed at said at least one purifier, said sensor being suitable to detect a volume of purified air in a given time interval;
    a dedicated server suitable to receive data of the detected volume of purified air from said sensor and store said data in a special memory; and
    at least one manager user of the system suitable to access, by means of pre-set credentials, the data of the detected volume of purified air stored in said special memory by means of any electronic device connected to the internet or to a local network connected to said dedicated server.

2. The indoor and outdoor air purification system according to claim 1, wherein the indoor and outdoor purifier further comprises:
    a guard (1) suitable to surround and protect all components of said purifier; said guard (1) being openable or removable to allow access and replacement of the components kept therein;
    a pair of grids (2-2') including an upper grid (2) and a lower grid (2') with respect to said guard (1) suitable to allow the inflow of air to be treated and the outflow of the purified air from inside said purifier;
    a base (4) suitable to stabilise said purifier on the ground;
    an upper lid (3) suitable to protect the internal of said purifier against external agents and against the fall of objects into said purifier;
    a system of internal supports (5) suitable to be engaged with all the internal and external components of said purifier to maintain the stability and the correct position.

3. The indoor and outdoor air purification system according to claim 1, wherein each surface of the indoor and outdoor air purifier, except for surfaces of said filters (8), is painted with a nano-coating suitable to preserve said surfaces against oxidation, corrosion, chemical attacks and acts of vandalism.

4. The indoor and outdoor air purification system according to claim 1, wherein the indoor and outdoor air purifier further comprises a remote-settable timer suitable to actuate and block said fan (7) at pre-established times.

5. The indoor and outdoor air purification system according to claim 2, wherein said guard (1) is transparent or translucent.

6. The indoor and outdoor air purification system according to claim 2, further comprising, at the external surface of said guard (1), at least one LED light suitable to light the surrounding space when said purifier is active.

7. The indoor and outdoor air purification system according to claim 1, wherein
    the LED lights (9) are switchable to provide light from the interior of the air treatment duct (6) to the external environment so that the air purifier operates as a lamp, and
    the air purifier is externally covered by a plurality of strips (10-10'-10"), such that when the LED lights (9) are switched to provide the light from the interior of the air treatment duct (6) to the external environment, the strips modulate and filter the light coming from said LED lights (9) to the external environment so that the air purifier operates as the lamp.

8. The indoor and outdoor air purification system according to claim 1, wherein the air purifier is capable of reducing at least the following toxic substances:
    inorganic compounds;
    chlorinated organic compounds;
    organic compounds;
    pesticides;
    bacteria;
    virus;
    transforming the toxic substances, through said photocatalysis process, into limestone, sodium nitrates and nitrites, calcium nitrates and nitrites, sodium carbonate and salts.

9. The indoor and outdoor air purification system according to claim 1, wherein the system comprises a plurality of the purifiers.

10. The indoor and outdoor air purification system according to claim 1, further comprising at least one timer, installed in each purifier, suitable to be remote-set to manage the operating and stop cycles of each purifier comprised in said system.

11. The indoor and outdoor air purification system according to claim 1, wherein installed at each filter (8) of each purifier is a sensor suitable to detect the amount of toxic and/or pollutant substances withheld in said filter (8), said sensor being suitable to send the detected data to said dedicated server to allow the manager user to know the residual efficiency of each filter (8) of each purifier and, thus, schedule maintenance thereof.

12. The indoor and outdoor air purification system of claim 8, wherein the indoor and outdoor air purifier is capable of reducing NOX; SOX; CO; $NH_3$; $CH_3S$; and $H_2S$.

13. The indoor and outdoor air purification system of claim 8, wherein the indoor and outdoor air purifier is capable of reducing $CH_2Cl_2$; $CHCl_3$; $CCl_4$; 1,1-$C_2H_4Cl_2$; 1,2-$C_2H_4Cl_2$; 1,1,1-$C_2H_3Cl_3$; 1,1,2-$C_2H_3Cl_3$; 1,1,1,2-$C_2H_2Cl_4$; 1,1,2,2,-$C_2H_2Cl_4$; 1,2-$C_2H_2Cl_2$; $C_2HCl_3$; $C_2Cl_4$; dioxins; chlorobenzene; and chlorophenol.

14. The indoor and outdoor air purification system of claim 8, wherein the indoor and outdoor air purifier is capable of reducing $CH_3OH$; $C_2H_5OH$; $CH_3COOH$; $CH_4$; $C_2H_6$; $C_3H_8$; $C_2H_4$; $C_3H_6$; $C_6H_6$; phenol; toluene; ethylbenzene; o-xylene; m-xylene; and phenanthraquinone.

15. The indoor and outdoor air purification system of claim 8, wherein the indoor and outdoor air purifier is capable of reducing triadimefon; pirimicarb; asulam; diazinon; MPMC; and atrazine.

16. The indoor and outdoor air purification system according to claim 2, wherein each surface, except for those of said filters (8), is painted with a nano-coating suitable to preserve said surfaces against oxidation, corrosion, chemical attacks and acts of vandalism.

17. The indoor and outdoor air purification system according to claim 2, further comprising a remote-settable timer suitable to actuate and block said fan (7) at pre-established times.

18. The indoor and outdoor air purification system according to claim 3, further comprising a remote-settable timer suitable to actuate and block said fan (7) at pre-established times.

* * * * *